United States Patent
Faber et al.

[11] Patent Number: 6,037,183
[45] Date of Patent: Mar. 14, 2000

[54] AUTOMOTIVE HYDROCARBON SENSOR SYSTEM

[75] Inventors: Margaret K. Faber, Corning; Yuming Xie, Painted Post, both of N.Y.

[73] Assignee: Corning Incorporated, Corning, N.Y.

[21] Appl. No.: 08/980,346

[22] Filed: Nov. 28, 1997

Related U.S. Application Data

[60] Provisional application No. 60/033,142, Dec. 20, 1996, and provisional application No. 60/033,141, Dec. 20, 1996.

[51] Int. Cl.$^7$ .......................................................... F01N 3/10
[52] U.S. Cl. .......................... 436/137; 436/143; 436/118; 422/83; 422/94; 422/98
[58] Field of Search ...................................... 436/116, 118, 436/137, 143; 422/51, 83, 94–98; 50/274–277

[56] References Cited

U.S. PATENT DOCUMENTS

| | | |
|---|---|---|
| 2,980,743 | 4/1961 | Toft . |
| 3,560,160 | 2/1971 | Lanneau . |
| 3,898,161 | 8/1975 | Barker . |
| 3,906,721 | 9/1975 | Micheli et al. . |
| 3,914,376 | 10/1975 | Barker . |
| 4,006,103 | 2/1977 | Meguerian et al. . |
| 4,012,485 | 3/1977 | Meguerian et al. . |
| 4,036,592 | 7/1977 | Brown et al. . |
| 4,128,506 | 12/1978 | Hegedus et al. . |
| 4,256,985 | 3/1981 | Goodson et al. . |
| 4,289,737 | 9/1981 | Acres et al. . |
| 4,975,406 | 12/1990 | Frestad et al. . |
| 5,157,204 | 10/1992 | Brown et al. . |
| 5,177,464 | 1/1993 | Hamburg . |
| 5,255,511 | 10/1993 | Maus et al. . |
| 5,265,417 | 11/1993 | Visser et al. . |
| 5,314,828 | 5/1994 | Dalla Betta et al. . |
| 5,408,215 | 4/1995 | Hamburg . |
| 5,444,974 | 8/1995 | Beck et al. . |
| 5,472,580 | 12/1995 | Kennard, III et al. . |
| 5,486,336 | 1/1996 | Dalla Betta et al. . |
| 5,494,826 | 2/1996 | Stetter et al. . |
| 5,560,200 | 10/1996 | Maus et al. . |
| 5,597,772 | 1/1997 | McCabe et al. . |

FOREIGN PATENT DOCUMENTS

| | | |
|---|---|---|
| 0 358 925 | 3/1990 | European Pat. Off. . |
| 0 751 390 | of 1997 | European Pat. Off. . |
| 0 751 390 | 1/1997 | European Pat. Off. . |
| 1 286 863 | 8/1972 | United Kingdom . |

*Primary Examiner*—Lyle A. Alexander
*Attorney, Agent, or Firm*—Timothy M. Schaeberle

[57] ABSTRACT

A system for measuring the non-methane HC concentration of gas sample, e.g. automotive exhaust gas, comprising first and second catalytic differential calorimetric sensors. The first catalytic differential calorimetric sensor is capable of producing a first output signal representative of the exothermic effect of the oxidation of the predominate oxidizable species ($CO+H_2$+non-methane HC combination) in the gas sample. The second catalytic differential calorimetric sensor is capable of producing a second output signal representative of the exothermic effect of the combined oxidation of the $CO+H_2$+alkene hydrocarbon species in the gas sample. Lastly, the system includes a means for comparing the first output signal with the second output signal, thereby indicating the total concentration of unburned aromatic and alkane hydrocarbon species in the gas sample which directly correlates to the total non-methane HC concentration. A method carried out by the system comprises the following steps: (a) contacting a first portion of an exhaust gas with a sensor and producing an output signal representative of the concentration of the predominate ($CO+H_2$+non-methane HC species) oxidizable species in the exhaust gas; (b) contacting a second portion of the exhaust gas with a second sensor and producing a second output signal representative of the combined concentration of $CO+H_2$+alkene hydrocarbon species in the second exhaust gas portion; and (c) determining the aromatic and alkane hydrocarbon species concentration, and thus the total non-methane HC concentration, of the exhaust gas by comparing the first output signal with the second output signal.

17 Claims, 5 Drawing Sheets

AUTOMOTIVE HYDROCARBON SENSOR SYSTEM

This application claims the benefit of U.S. provisional application Ser. No. 60/033,142, filed Dec. 20, 1996, entitled "AUTOMOTIVE HYDROCARBON SENSOR SYSTEM" by Margaret K. Faber and Yuming Xie, and 60/033,141, filed Dec. 20, 1996, entitled RHODIUM CATALYST FOR PURIFYING EXHAUST GASES, by Yuming Xie.

BACKGROUND OF THE INVENTION

1. Field of the Invention

The present invention relates generally to the technology of measuring the non-methane hydrocarbon concentration in the emissions of an automotive internal combustion engine, and more particularly to the use of catalytic differential calorimetric sensors to monitor the non-methane hydrocarbon oxidation efficiency of an exhaust system's catalytic converter.

2. Description of the Related Art

Catalytic converters have been used on gasoline-fueled automobiles produced in the United States since the mid-1970's for the purpose of promoting the oxidation of unburned hydrocarbons (HCs) and of carbon monoxide (CO). Soon after their introduction, the converters were adapted to promote the chemical reduction of oxides of nitrogen ($NO_x$). At the present time these converters typically employ small amounts of platinum, palladium and rhodium dispersed over a high surface area particulate carrier vehicle which, in turn, is distributed as a thin, porous coating (sometimes called a washcoat) on the wall of a ceramic monolith substrate. The substrate is typically formed by an extrusion process providing hundreds of thin wall, longitudinal parallel open cells per square inch of cross section. These flow-through catalytic devices are housed in a suitable stainless steel container and placed in the exhaust stream under the vehicle downstream from the engine's exhaust manifold Under warm, steady-state engine conditions, this conventional catalytic converter containing the precious metal based three-way catalyst (TWC), so called because it simultaneously affects the oxidation of CO and unburned HCs and the reduction of $NO_x$, effectively and efficiently removes most of the automotive emissions. However, the catalyst system may become malfunctioning after experiencing thermal aging at an unusually high temperature, high exposure to poisoning gases like $SO_2$, and Pb, etc. Furthermore, new emissions regulations require an extended durability of the catalytic converter from 50,000 miles to 100,000 miles Lastly, as a means to ensure that vehicles meet the certified emission standards throughout the vehicle's operation life, On-Board Diagnostics-II (OBD-II) regulation, as passed by the California Air Resource Board (CARB), calls for continuous monitoring of the efficiency of catalytic converters by direct measurement of the hydrocarbon emission in the exhaust system after the catalyst light-off. Specifically, the monitoring system should be able to indicate when the catalyst system is malfunctioning and its conversion capability has decreased to the point where either of the following occurs: (1) HC emissions exceed the applicable emission threshold of 1.5 times the applicable Federal Test Procedure (FTP) HC standard for the vehicle, and (2) the average FTP Non-methane Hydrocarbon (NMHC) conversion efficiency of the monitored portion of the catalyst system falls below 50 percent.

On the other hand, automotive emissions before the catalyst system has warned up to operational temperatures, namely, cold start emissions comprise the majority of pollution from automobiles. Approaches such as, catalytic converters, close coupled to the engine, which heat and begin to function within a few seconds, electrically heated catalytic converters and in-line adsorbers which temporarily store unburned hydrocarbons until the catalytic converter lights off, have all been proven to be effective solutions for the reduction of cold start emissions. Again, OBD-II regulations require that systems be installed in the exhaust system to directly monitor the functional status of any of these "cold-start" devices during the lifetime of the car (100,000 miles).

The use of hydrocarbon sensors as on-board catalytic efficiency monitors is a relatively new technological area which has generated increasing interest for the auto industry as a result of OBD-II legislation. Generally, the use of a catalytic calorimetric sensor, which measures the effect of the exotherm of the catalyzed oxidation of the oxidizable species including hydrocarbons over supported precious metal catalysts on the resistance of a coil conductor is known.

U.S. Pat. No. 5,408,215 (Hamburg et al.) generally discloses a system comprising: (1) a test chamber remote from the engine exhaust gas stream, (2) means for alternately supplying the chamber with an upstream and a downstream exhaust gas stream sample; (3) a hydrocarbon sensor exposed to the exhaust gas samples in the chamber to produce a signal responsive to the concentration of hydrocarbon in the chamber, and, (4) a means for comparing the downstream and upstream signals to produce a sensed signal for comparison with a reference signal to determine if the converter is faulty.

U.S. Pat. No. 5,265,417 (Visser et al.) discloses a method comprising the steps of: (1) determining the hydrocarbon concentration of the exhaust gas upstream and downstream of the converter by alternately sampling the upstream and downstream exhaust gas and passing the samples to a catalytic differential calorimetric sensor; (2) comparing the hydrocarbon content of the upstream and downstream exhaust gas samples and thereby determining the hydrocarbon conversion efficiency of the catalytic converter.

A shortcoming common to both Visser and Hamburg is the necessary measurement of both an upstream and downstream exhaust gas sample at a position remote from the exhaust gas stream. This is accomplished through the use of a combination of a remote sensing chamber and a valving and delivering system which is capable of delivering alternate samples of the upstream and downstream exhaust As a result of the complexity of these systems they exhibit an increased possibility of system failure during the lifetime of the vehicle; e.g., dirty and/or rusty valving may decrease the accuracy of the HC measurement.

Lastly, U.S. Pat. No. 5,444,974 (Beck et al.) discloses a method diagnosing the performance of the catalytic converter for the oxidation of CO and HC involving producing an electrical signal from a calorimetric sensor located in the exhaust stream downstream of the catalytic converter. The calorimetric sensor is comprised of a first portion bearing an oxidized catalyst for CO, $H_2$ and HC and an adjacent second portion that is oxidation catalyst-free.

Common to all three of these systems is the disclosure of a non-selective or "total" sensor which not only measures the HC species but also the CO and $H_2$ species present in the exhaust gas. All three references teach the use of a calorimetric sensor, while Hamburg and Visser additionally disclose the use of a semiconductor-type with a material that adsorbs gases; none of the references provide any teaching as to how to make the sensors selective for HCs alone. Given the fact that a properly functioning catalytic converter, after light-off, typically produces an exhaust gas hydrocarbon concentration, which is typically on the order of tens (or below) ppm, while the CO concentration is typically an order of a magnitude greater, none of these diagnostic systems are capable of directly and selectively measuring HC concentration in this concentration range. Specifically, these sensor systems do not compensate or account for these interfering gases, especially the CO, which are present in concentrations far greater than the HC species. As such, the systems exhibit a reduced ability to accurately measure the HC concentration.

SUMMARY OF THE INVENTION

Accordingly, the present invention, in its broadest sense, is directed at a system and a method for selectively and directly measuring the non-methane hydrocarbon (HC) concentration in a gas sample; e.g., the exhaust gases produced by an internal combustion engine. In either the method or the system, the hydrocarbon sensor used is capable of detecting, under a variety of engine and fuel conditions, including cold start conditions, low (ppm) concentrations of non-methane HCs in exhaust gases containing a variety of gaseous components, in addition to the hydrocarbons. The location of the system, or performance of the method, at a location downstream of a catalytic converter, results in a configuration which has particular utility in catalytic converter efficiency monitoring.

Simply stated, the system for measuring the non-methane HC concentration of gas sample comprises first and second catalytic differential calorimetric sensors, the outputs of which are compared to generate the hydrocarbon concentration in the gas sample. The first catalytic differential calorimetric sensor is capable of producing a first output signal representative of the exothermic effect of the oxidation of the predominate oxidizable species in the gas sample, predominate oxidizable species comprising a combination of $CO+H_2$+non-methane HC. The second catalytic differential calorimetric sensor is capable of producing a second output signal representative of the exothermic effect of the combined oxidation of the $CO+H_2$+alkene hydrocarbons in the gas sample. Lastly, the system includes a means for comparing the first output signal with the second output signal thereby indicating the total concentration of unburned aromatic and alkane hydrocarbon species in the gas sample which directly correlates to the total non-methane HC concentration.

In one embodiment, the system, incorporated within an internal combustion engine's exhaust system, includes a first catalytic differential calorimetric sensor comprising a substrate having a first catalytic portion having an oxidation catalyst capable of oxidizing the predominate oxidizable species in a first exhaust gas portion and an adjacent second reference portion which is oxidation catalyst-free. Additionally, the system includes a second catalytic differential calorimetric sensor comprised of a substrate having a first catalytic portion having an oxidation catalyst capable of the selective oxidation of the $CO+H_2$+alkene HCs in a second exhaust gas portion, and an adjacent second reference portion which is oxidation catalyst-free.

In its simplest form, the method of measuring the hydrocarbon concentration of exhaust gases comprises the following steps: (a) contacting a first portion of the exhaust gas with a sensor and producing an output signal representative of the concentration of the predominate oxidizable species in the exhaust gas portion, the predominate oxidizable species including the $CO+H_2$+non-methane HC combination; (b) contacting a second portion of the exhaust gas with a second sensor and producing a second output signal representative of the combined concentration of $CO+H_2$+alkene HC in the second exhaust gas portion, and (c) comparing the first output signal with the second output signal thereby determining the aromatic and alkane HC concentration, and thus the total exhaust gas HC concentration.

DETAILED DESCRIPTION OF THE INVENTION

Apparatus

The present invention is directed at a system for measuring the hydrocarbon concentration of a gas sample. In its simplest embodiment the system comprises a first and a second catalytic differential calorimetric sensor, each capable of producing an output signal representative of an oxidation exothermic effect. The first sensor's signal is representative of the oxidation of the predominate oxidizable species ($CO+H_2$+non-methane hydrocarbons) in a gas sample while the second signal is representative of the oxidation of the $CO+H_2$+alkene hydrocarbons species in the gas sample.

Additional features of the system includes the following: (1) a heater for maintaining each of the sensors at a sufficient temperature to ensure the respective oxidations—specifically the oxidation of the predominate oxidizable species and the $CO+H_2$+alkene hydrocarbon combination, respectively; and, (2) a means for comparing the first and second output signals to indicate the total concentration of unburned aromatic and alkane hydrocarbons in the gas sample—which directly correlates to the total hydrocarbon concentration. Hydrocarbons (HC), as oxidized and measured herein refers to non-methane hydrocarbons.

Figure 1:
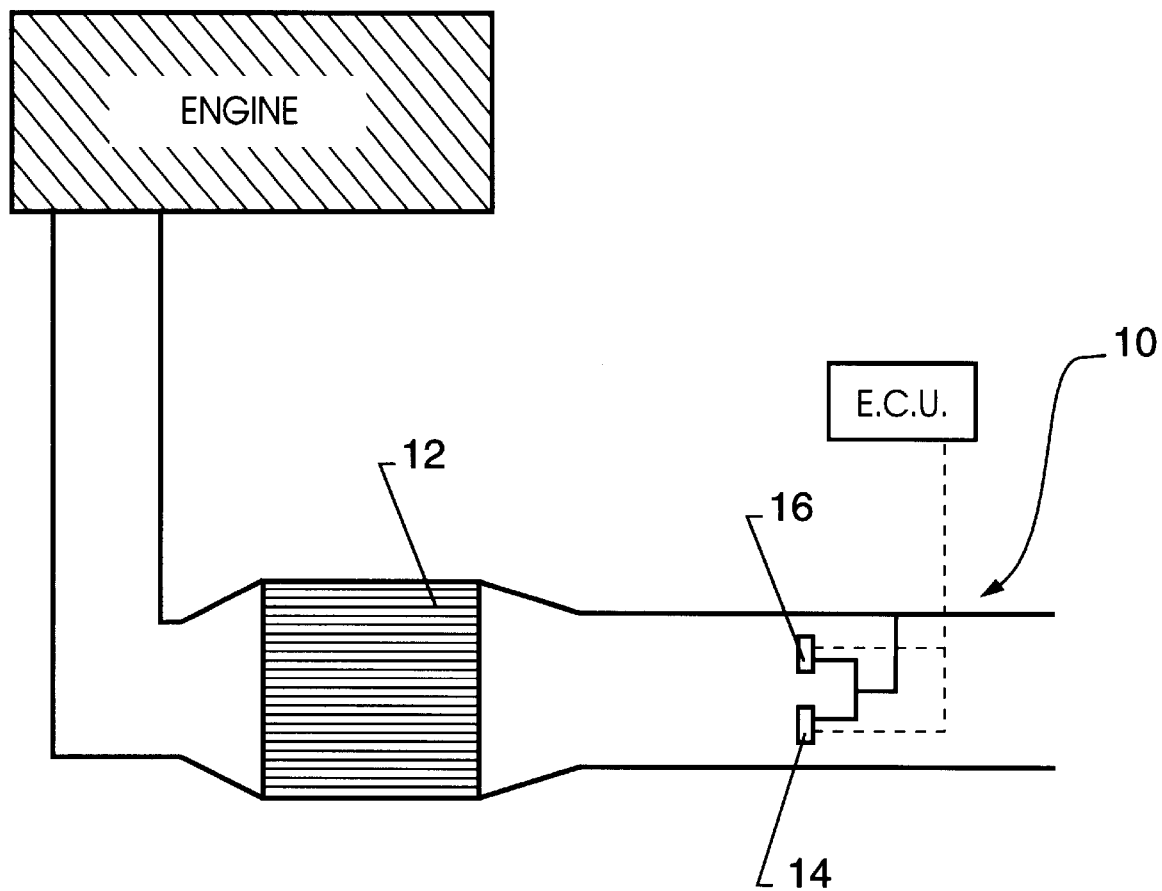
FIG. 1 is a schematic diagram of an embodiment of the inventive system for measuring hydrocarbon concentration of an exhaust gas stream.

Referring to FIG. 1, illustrated therein is a schematic representation of one embodiment of the system 10 for measuring the HC concentration of exhaust gases in an exhaust stream, according to one embodiment of the present invention. A catalytic converter 12 is located in the exhaust gas downstream of an internal combustion engine. This converter 12 is capable of catalyzing the exhaust gas so as to reduce the pollutants present in the exhaust gas. Preferably, the catalyst is a three-way catalyst which functions to oxidize both HCs and CO, as well as to reduce $NO_x$, in the exhaust gas. The monitoring system 10 uses catalytic differential calorimetric sensors to directly measure the HC concentration in the exhaust gas.

Referring still to FIG. 1, the monitoring system 10 includes a first catalytic differential calorimetric sensor 14 and a second catalytic differential calorimetric sensor 16, both of which are in contact with the exhaust gas at a position downstream of the catalytic converter 12; however, the sensors could both be located upstream, or alternately upstream and downstream, of the catalytic converter.

Figure 2:
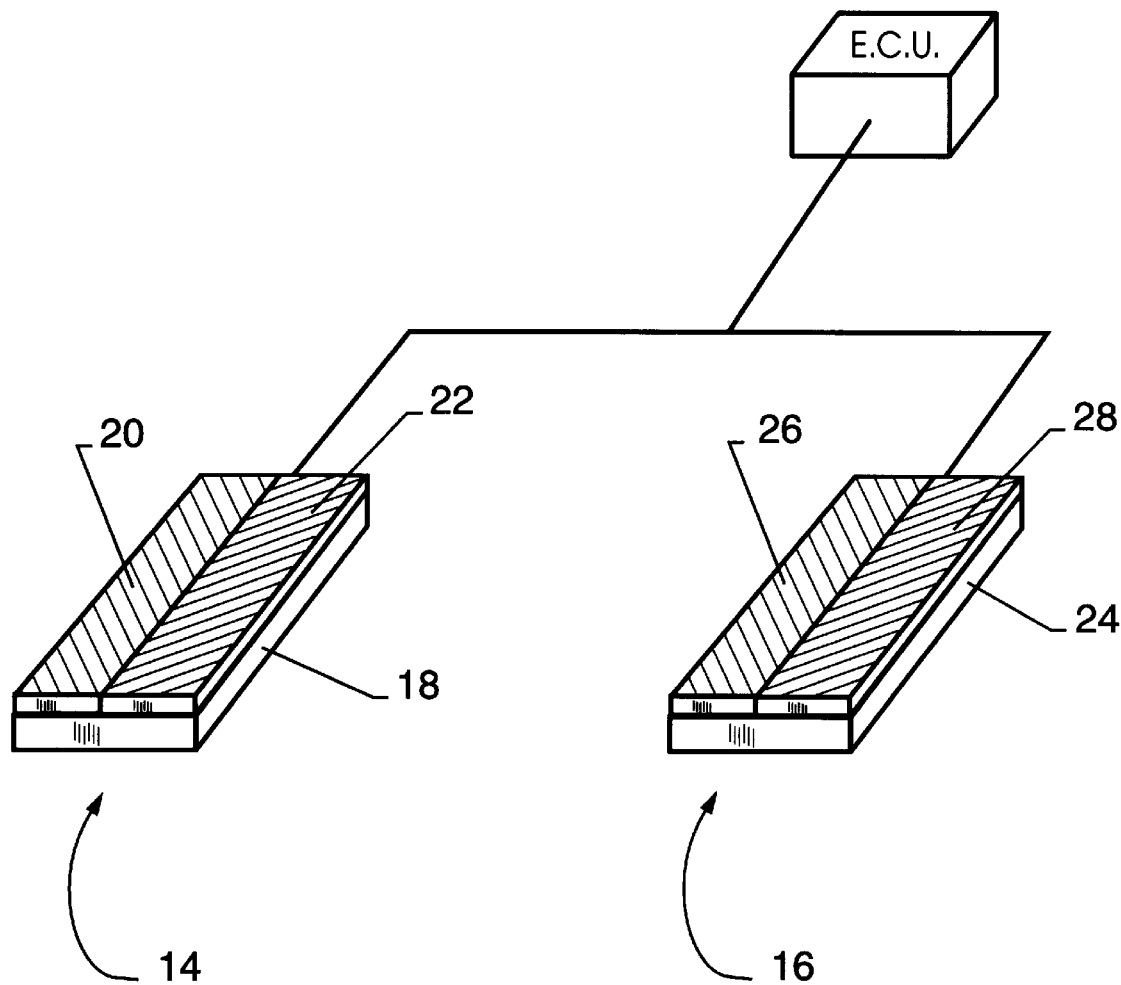
FIG. 2 is a schematic diagram of the catalytic differential calorimetric hydrocarbon sensor described herein.

Referring now to FIG. 2 illustrated therein is a schematic perspective view of the general sensor system which is utilized in the instant invention. First catalytic differential calorimetric sensor 14 is a divided sensor device, a portion of which is catalytically active. First sensor 14 is comprised of a substrate 18 comprising a first portion 20 having deposited thereon an oxidation catalyst comprising a catalyst-support material and a catalytically active precious metal capable of oxidizing the predominate oxidizable species in a portion of the exhaust gas; i.e., a "predominate oxidation species" catalyst sensor. First sensor 14 further comprises an adjacent second reference portion 22 having deposited thereon an un-catalyzed support material. Oxidation of the predominate oxidizable species (HCs, CO and $H_2$), an exothermic reaction in which energy is released, will raise the temperature of the first catalytic portion 20 above that of the non-catalyzed second reference portion 22. Furthermore, the sensor 14 includes a heater (not shown) for maintaining the catalyzed and the reference portions of the first sensor at a constant, elevated temperature, sufficient to ensure that the catalytic oxidation process occurs, i.e., substantially complete oxidation of the predominate oxidizable species. Lastly, it is self evident that the sensor 14 also includes a means (not shown) for generating the first output signal representative of the exothermic effect occurring as a result of the oxidation of the predominate oxidizable species in the exhaust gas portion. For instance, this can simply consist of a temperature measuring device which measures the temperatures of both the first portion and the reference second portion (the first output signal), a comparison of which would be representative of the first exothermic effect.

Suitable catalyst-support materials include any high surface area material, preferably a ceramic material, including for example, silica, alumina, zirconia, ceria or combinations thereof As these are catalytic oxidation sensors and normal engines typically operate at a stoichiometric air/fuel ratio, excess oxygen is required to ensure that the catalytic reaction occurs and thus the sensor functions properly. Although excess oxygen can be supplied by providing an air supply line, or the like, to the exhaust gas, it is preferred that the excess oxygen be supplied through the use of a catalytic-support material which is comprised of oxygen storage material. In this case, the catalyst-support material is capable of storing and releasing oxygen depending upon the widely and rapidly varying oxygen concentration in the exhaust stream. Furthermore, use of oxygen storage materials as the catalyst-support material ensures that the catalytic calorimetric sensors will function properly (i.e., substantially complete oxidation of the predominate oxidizable species) even under fuel-rich conditions. This being said it, is preferred that the catalyst-support material be comprised of a ceria-containing material, most preferred that of a ceria-zirconia solid solution.

Any precious metal which is capable of oxidizing CO, $H_2$, and non-methane HC, i.e., the predominate oxidizable species, present in the gas sample portion would be suitable for use in the oxidation catalyst of the instant invention; suitable precious metals include materials such as rhodium, platinum, palladium, iridium, silver, gold, ruthenium, osmium, and mixtures thereof Preferably, the precious metal material for first catalytic calorimetric sensor 14 comprises platinum or palladium, as well as mixtures thereof.

Second catalytic differential calorimetric sensor 16 is also a divided sensor device, again, a portion of which is catalytically active, Second sensor 24 is comprised of second substrate 24 comprising a first portion 26 upon which is deposited an oxidation catalyst comprising a catalyst-support material and a catalytically active precious metal which is capable of selectively oxidizing a combination of $CO+H_2$+alkene hydrocarbon species in a second portion of the exhaust gas; i.e., a "selective" oxidation catalyst sensor. Second sensor 24 also comprises an adjacent second reference portion 28 comprising an uncatalyzed catalyst-support material. The oxidation catalyst precious metal utilized is one which selectively oxidizes CO, $H_2$ and alkene hydrocarbons but which does not oxidize the aromatic and alkane hydrocarbons. This oxidation of the species in the second portion of the exhaust gas (i.e., CO, $H_2$ and alkene hydrocarbons), is again an exothermic reaction in which energy is released which will raise the temperature of the catalyzed portion above that of the non-catalyzed portion. Furthermore, the second sensor 16 possesses a heater (not shown) for maintaining the catalyst and reference portions of the sensor at a temperature sufficient to substantially oxidize the $CO+H_2$+alkene hydrocarbons. Like the first sensor this sensor includes a means (not shown) for generating the second output signal representative of the second exothermic effect occurring as a result of the selective oxidation. Again, this can simply consist of a temperature measuring device which measures the temperatures of the first portion and reference second portion (the second output signal), a comparison of which would be representative of the second or selective exothermic effect; i.e., the exothermic effect of oxidizing the $CO+H_2$+alkene species.

As before, suitable catalyst support materials for the second sensor include any high surface area material, preferably a ceramic material, including for example, silica, alumina, zirconia, ceria, ceria-stabilized zirconia, titania, and mixtures thereof As indicated above is it is essential that the oxidation catalyst which is used on the catalytic portion of the second sensor is one which selectively oxidizes the $CO+H_2$+alkene species combination. One such oxidation catalyst is comprises an amount of highly dispersed Rh-cluster deposits on a high surface area catalyst-support material, preferably silica. The oxidation catalyst according to the invention should be prepared in accordance with a method which ensures that the Rh-cluster deposits on the high surface area catalyst-support material are highly dispersed. Specifically, "highly-dispersed" as used herein, refers to Rh-cluster deposits covering no greater than about 10% of the surface area of the support material, preferably no greater than about 5% of the surface area of the support material. Furthermore, the method of catalyst preparation should ensure that the Rh-cluster deposits exhibit the proper size, as deposited on the surface catalyst-support material. The Rh-cluster deposits, comprised of a single rhodium atom or a cluster of at least two Rh atoms which, should exhibit a diameter of less than about 5 nm, preferably less than about 1 nm, most preferably less than about 5 Å. If the Rh-deposits are too closely spaced together they will effectively function as if a precious metal layer is deposited on the support material surface, the result being a loss of the selective oxidation feature which is obtained as a result of the small size and high dispersion of the Rh-deposits.

In addition to the aforementioned limitation on the surface area coverage of the Rh-cluster deposits, which exhibit a hemispherical-like shape on the catalyst support surface, it is critical that the total amount of rhodium comprise an amount on the catalytic-support material, which will be sufficient to provide a small but catalytically effective amount of the rhodium metal to substantially and completely catalyze the $CO+H_2$+alkene HCs in an exhaust gas portion. For example, the total amount of Rh which should be deposited on a catalyst-support having an approximate area of 150 $m^2$/g, should be less than about 0.3%, by weight, of the total oxidation catalyst weight, and preferably, less than about 0.1%, by weight of the total oxidation catalyst. This small amount of Rh loading ensures that the Rh clusters remain highly dispersed and thus the Rh-containing catalyst remains highly selective.

In these catalysts the precious metal rhodium component is the main catalytically active component in the catalytic reaction, and it is the principal aim of the highly dispersed and small sized rhodium to contribute to ability of oxidation catalyst to selective oxidize the $CO+H_2$+alkene HC species. While not intending to be limited by the theory it is thought that the selective nature of the inventive rhodium-containing oxidation catalyst is based on a combination of the highly dispersed nature and small size of the rhodium cluster deposits which are deposited on the surface of the catalytic-support material.

The "catalyst-support material", a powdered material with a high specific surface area, upon which the precious metal rhodium is applied provides support for the highly-dispersed Rh-metal clusters. Suitable catalyst-support materials include materials selected from the group consisting of silica, alumina, titania, zirconia, zeolite materials as well as mixtures thereof For the following reasons, silica comprises the preferable catalyst-support material: (1) silica ($SiO_2$) is more acidic and thus exhibits a reduced affinity, when compared to alumina, titania and zirconia, for attracting the $SO_2$ molecule, therefore reducing $SO_2$ concentration over the $SiO_2$ surface which directly results in less contact of $SO_2$ with the active Rh site (poisoning); (2) silica exhibits a greater static reaction effect, thus resulting in a greater ability to hold the Rh-cluster deposits in highly dispersed states. Alumina is suitable for use as the catalytic support material, however, it has stronger interaction with $SO_2$ thus $SO_2$ has a more profound poisoning effect on the catalytic activity. As such, an alumina supported Rh-catalyst would require a higher operating temperature thus resulting in a smaller "window" for oxidation to occur before the HCs begin to self ignite; as compared to a catalytic "window" for the preferred catalytic-support material, silica.

A suitable procedure for preparing the Rh-containing catalyst, so as to ensure high dispersion, small sized Rh-cluster deposits on the surface of the catalytic-support material, in accord with the present invention generally involves the following steps: (1) adding Rh-containing compound (e.g. rhodium chloride) to a solvent (e.g., $H_2O$) to form a Rh-containing solution and thereafter adding an adequate amount of an ammonium-containing solution (e.g. $NH_4OH$) to form an Rh-ammonium solution; (2) impregnating an amount of a high surface area catalyst-support material powder with the Rh-ammonium solution by incipient wetness impregnation and thereafter drying and calcining this impregnated powder to form a dry powder mixture comprised of the high surface area catalytic-support material with highly dispersed Rh-deposits located on the surface.

A variety of Rh-containing compounds may be used in the above procedure including the nitrates, halides, acetonulacetonates or appropriate rhodium carbonyls, in other words any rhodium-containing material can be used as long as the results is small sized, highly dispersed Rh-cluster deposits.

As described above, each of the two above-described sensor designs employs some means for measuring the extent of the exotherm; i.e., a means for measuring the increase in the temperature of the oxidizing portion, as well the reference temperature of the non-oxidizing/reference portion which remains unchanged after the oxidation. In sum, the temperatures are measured so as to calculate the following (1) the difference between the temperatures of the catalyzed (increased as result of catalytic oxidation) and the un-catalyzed portions (constant reference temperature which remains unchanged throughout the catalytic oxidation) of the first sensor which is a measure of the exothermic effect, of the oxidation of the predominate oxidizable species in a portion of the exhaust gas sample—$\Delta T_1=[HC+CO+H_2]$; and, (2) the difference between the temperatures of the catalyzed (increased as result of catalytic oxidation) and the uncatalyzed portions (constant reference temperature which remains unchanged throughout the catalytic oxidation) of the second sensor which is a measure of exothermic effect of catalytic oxidation of substantially all the oxidizable species except aromatic and alkane hydrocarbon species in another portion of the exhaust gas sample—$\Delta T_2=[CO+H_2+alkenes]$.

The temperature measuring device may be well known devices such as thermistors, or thermocouples which are incorporated within the aforementioned substrate and which are capable of detecting the temperature of the reference portion and the temperature rise of the catalyzed portion, occurring as a result of the oxidation reactions described above, the difference being the result of the oxidation exotherm. If thermocouples or thermopiles are used, the sensor devices would require a separate heater, e.g., a heating coil which would maintain the oxidation catalyst at the aforementioned temperature sufficient to effect substantially complete oxidation.

In another embodiment a resistance-temperature detectors (RTD) would be incorporated into each of the catalytic and reference portions of the substrate of each respective sensors; the RTD would perform dual functions of heating and maintaining the catalyst portion at a temperature sufficient to effect substantially complete oxidation, as described above. Specifically, each of the RTDs would be operated by heating the substrate to a set temperature by passing a current to each and thereafter measuring the difference in required current necessary to maintain the set temperature of the oxidation and reference RTD; this difference would a measure of the oxidation exotherm occurring as result of whichever oxidation reaction is occurring.

Regardless of the means used to measure the respective temperatures, these measured temperatures are converted to an electrically measurable quantity (voltage, resistance, current etc.) by the temperature measuring means and thereafter compared to generate the first and second output signals, which are thereafter compared to arrive at the aromatic and alkane hydrocarbon concentration and thus the total hydrocarbon concentration. It is contemplated that a microprocessor based electronic control unit (ECU) can be used as the aforementioned means to compare the measurable temperature outputs to generate the first and second exothermic output signals of the first and second catalytic differential calorimetric sensors. The ECU would thereafter compare the first and second exotherms to indicate the aromatic and alkane concentration and thereafter the total concentration of unburned hydrocarbons in the downstream exhaust gas.

In another embodiment, a system for measuring the HC concentration of a gas sample simply comprises the first and second sensor devices disposed on the same substrate; i.e., the first oxidation catalyst is placed adjacent the second oxidation catalyst. This embodiment is possible only if the precious metal of each of the first and second oxidation catalyst can be maintained at the same base temperature to achieve the substantial oxidation of the predominate oxidizable species and the $CO+H_2+$alkene hydrocarbons, respectively. In other words, since the respective oxidations occur at the same base temperature the "selective" oxidation catalyst can serve as the reference for comparison to the "predominate oxidizable species" oxidation catalyst.

Method

The present invention is also directed at a method of directly measuring the hydrocarbon concentration of the exhaust gases in the exhaust gas stream. Generally, the method involves the steps of contacting a first portion and a second portion of the exhaust gas with a first and second sensor, respectively. The output signals of the first and second sensors are then compared so as to determine the hydrocarbon concentration of the exhaust gas. In order to arrive at an accurate calculation of the hydrocarbon concentration, it is necessary that the first sensor be configured to produce an output signal representative of the predominate oxidizable species concentration in the first exhaust gas portion, while the second sensor is configured to produce a second output signal which is representative of the combined concentration of the $CO+H_2+$alkene hydrocarbon species in the second exhaust gas portion.

It should be noted that the portions can be measured in whatever manner is most practical, i.e., simultaneously, in series or in parallel assuming that the second portion has not already been subjected to catalytic oxidation. It is only important that each of the portions measured comprise substantially the same exhaust gas composition which is representative of the actual exhaust gas composition.

Having described in a general sense a method for directly measuring the hydrocarbon concentration, the following is a more detailed description of the steps of the method. The step of contacting a first exhaust gas portion with a sensor involves causing the gas portion to come into contact with a first catalytic differential calorimetric sensor and catalytically oxidizing the predominate oxidizable species present in the exhaust gas portion; the predominate oxidizable species includes CO, $H_2$ and non-methane hydrocarbons. The catalytic oxidation of the predominate oxidizable species, an exothermic reaction resulting in the release of heat, results in an increase in the temperature of at least the catalyzed portion of the sensor: $\Delta T_1 = [HC+CO+H_2]$. This exotherm is thereafter used for providing an output signal representative of the exothermic effect of the oxidation.

The step of contacting the second portion of exhaust with a sensor involves causing the gas to come into contact with a second catalytic differential calorimetric sensor and selectively oxidizing the combined $CO+H_2+$ alkene hydrocarbon species, present in the exhaust gas portion. Again the resultant oxidation reaction causes a temperature increase in at least the catalyzed portion of the sensor $\Delta T_2 = [CO+H_2+$alkenes$]$ which is thereafter used for producing a second signal representative of the second exothermic effect.

Lastly the first and second output signals, i.e., the first and second exotherms, are compared to generate the hydrocarbon concentration in the exhaust gas. Specifically, the combined aromatic and alkane hydrocarbon concentration in the exhaust gas is calculated by subtracting the exothermic effect contributed by the CO, $H_2$ and alkene oxidation from the exotherm of the predominate species oxidation: $[HC]=\Delta T_3=(\Delta T_1-\Delta T_2)$. In turn, this direct and selective measurement of aromatic and alkane HC concentration, in the presence of other oxidizable species such as CO and $H_2$ can thereafter be converted to generate the total non-methane HC concentration, assuming that there is a direct correlation between the aromatic and alkare hydrocarbon concentration and the total HC concentration (see description below).

Exhaust gas, for instance, contains greater than 200 species of HCs that can be divided into the alkene, alkane and aromatic species or families. Table I details a representative example of an engine exhaust data from a 1991 Buick Park Avenue automobile. The test was conducted in accordance with the FTP procedure for measuring accumulated engine exhaust emissions. Reported in Table I for the exhaust system test conducted are the following hydrocarbon emissions for the entire test cycle, reported in grams per mile: (1) the total non-methane hydrocarbons (NMHC); (2) the total alkene hydrocarbons; (3) the aromatic hydrocarbons; and, (4) the alkane hydrocarbons. Also reported are the percentage (%) of the total NMHC, which each of the hydrocarbon species alkene, aromatic, alkane and aromatic+alkane comprised. The two stages of the Bag I portion of the test comprised an initial or cold-start test stage (0–60 seconds), an intermediate stage (60–505 seconds), a Bag II stage followed which comprised a testing period of >250–1372 seconds.

TABLE I

|  | Initial Bag I Stage (cold-start: 0–60 secs.) | Intermediate Bag I Stage (60–505 secs) | Bag II Stage (506–1303 secs.) |
| --- | --- | --- | --- |
| Total NHMC (mg) | 1655 | 178 | 80 |
| Alkenes (mg) | 201 | 20 | 11 |
| Aromatics (mg) | 453 | 57 | 19 |
| Alkanes (mg) | 1001 | 101 | 50 |
| Alkane/NMHC (%) | 12 | 11.2 | 13.7 |
| Aromatic/NMHC (%) | 27.4 | 32 | 23.8 |
| Alkane/NMHC (%) | 60.6 | 56.8 | 62.5 |
| (Aromtic+Alkanes)/ NMHC (%) | 88 | 88.8 | 86.3 |

As is apparent from a study of the data set forth in Table I, car exhaust, during a typical FTP cycle, exhibits a composition in which the alkane and aromatic hydrocarbons account for greater than approximately 85% of the total HCs. Therefore, a selective HC sensor that detects only aromatics and alkanes with no interference from carbon monoxide or $H_2$ oxidation, is a practical device for measuring the total hydrocarbon concentration as there is a direct correlation between the combined aromatics and alkane concentration and the total HC concentration.

In the embodiment described above, when the exhaust gas portions measured are downstream of the catalytic converter, and therefore the hydrocarbon concentration of the exhaust gas is determined downstream of the catalytic converter, this measuring of the hydrocarbon concentration is, in actuality, a measure of how well the catalytic converter is functioning; i.e., a system for monitoring the performance of the catalytic converter efficiency. In other words, the concentration of the aromatic and alkane hydrocarbon present in the exhaust gas portions, downstream of the catalytic converter, directly correlates to the total HC (non-methane) concentration, i.e., the total non-methane HC tail pipe emissions. A measure of how well the catalytic converter is functioning would entail comparing this tail pipe emission to the certified FTP emission standards. As such, this method is a practical and accurate method for monitoring the hydrocarbon catalytic converter efficiency as required by OBD II.

EXAMPLES

Each of the following examples illustrate the fabrication of a sensor comprised simply of a pair of thermocouples as follows: (1) one uncatalyzed thermocouple, functioning as the aforementioned substrate, upon which is deposited a ceramic catalyst-support material which will generate a reference voltage/temperature, and (2) a second thermocouple, also functioning as the substrate, upon which is deposited a ceramic catalyst-support material and an appropriate precious metal catalyst material, and upon which the oxidation and temperature increase will occur.

Example 1

A first or "predominate oxidation species" sensor was prepared and tested in the following manner:

A ceria-stabilized zirconia/platinum powder mixture was prepared comprising a mixture consisting of 59.31 grams of cerium nitrate and 107.6 grams of zirconyl nitrate hydrate, both supplied by the Aldrich Chemical Company, Inc., Milwaukee, Wis. The mixture was dissolved in water to produce a 500 ml solution which was thereafter added dropwise to a 500 ml, 4N ammonium hydroxide aqueous solution. Following precipitation of cerium and zirconium hydroxides, the precipitate was thoroughly washed and thereafter dried overnight in an oven at 130° C. and thereafter calcined for four hours in stagnant air at a temperature of 500° C., to form ceria-stabilized zirconia.

Ten grams of the calcined ceria stabilized zirconia was "incipient wetness" impregnated with 3.0 g of hexachloroplatininc acid solution (Aldrich Chemical Company, Inc.) having a platinum content of about 10% by weight. The impregnated powder was again dried overnight in an oven at a temperature of 130° C. and thereafter calcined at 500° C. for four hours thereby forming a ceria stabilized zirconia material having 3% by weight Pt dispersed thereon.

The actual "predominate oxidation species" sensor was thereafter formed in the following manner:

An aqueous slurry comprised of the above calcined powder was formed and thereafter dip-coated as a 1 mm³ bead onto the tip of a type-K thermocouple, i.e., the first catalyzed portion. The second oxidation-catalyst-free portion also comprised a type K thermocouple which was dip-coated to form a 1 mm³ bead, however the bead consisted of a catalytically inactive $Al_2O_3$ material; the second or reference portion. Specifically, the catalytically inactive $Al_2O_3$ material comprised an aqueous slurry of Boehmite alumina, 20% by weight alumina, as manufactured by the PQ Corporation, Ft. Washington, Pa. Both coated thermocouples were thereafter rapidly dried by heating them with a heat gun exhibiting a temperature of approximately 350° C.

The two thermocouple pair forming the "predominate oxidation species" sensor was tested for oxidation response by placement in a tubular flow-through reactor by connecting them to a multi-pin feedthrough, Various reaction gas combinations were introduced into the reactor, via mass flow controllers, at a constant flow rate of 7508 cc/min. The furnace was heated to, and maintained throughout the testing, at a temperature of 440° C., resulting in a thermocouple temperature of 380° C. The base or initial reaction gas to which the various test gases (see below) were added consisted of 14% $CO_2$, 1% $O_2$, with the balance being made up of $N_2$.

Figure 3:
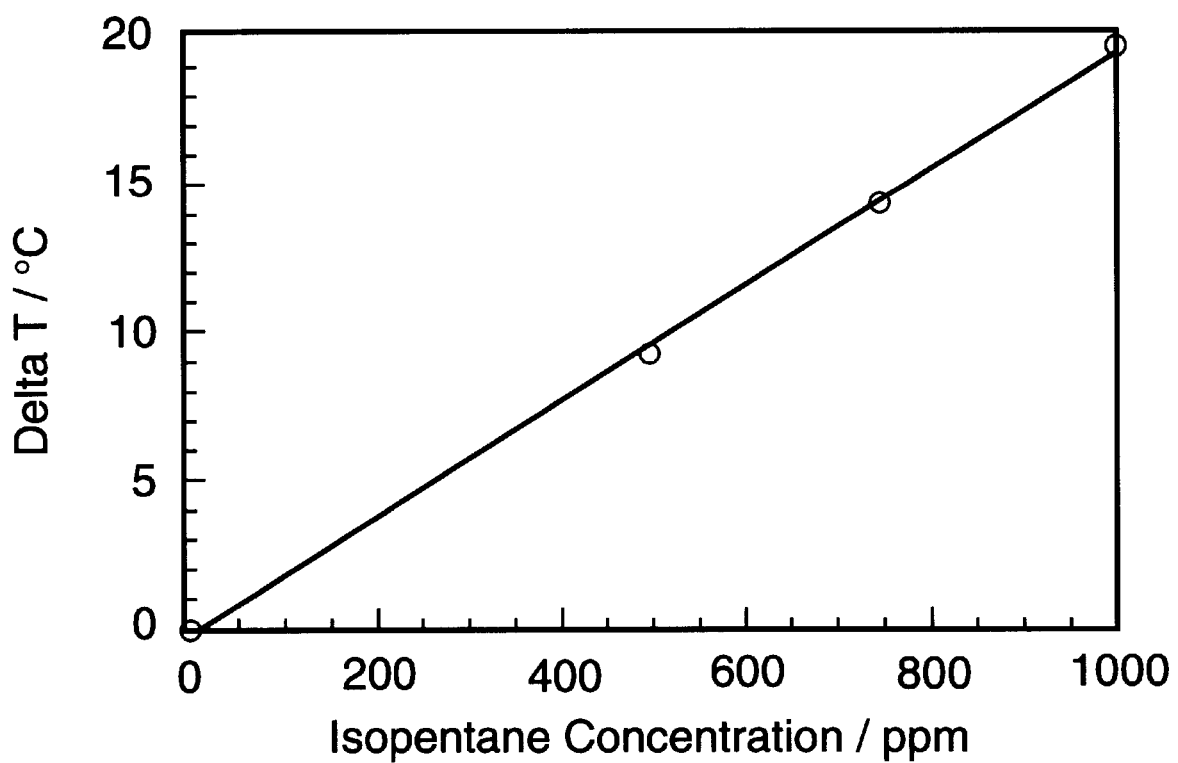
FIG. 3 is a graphical illustration of the temperature change ($\Delta T$) between a catalytic and reference thermocouple of a divided sensor device as a function of the isopentane (2-methyl-butane) concentration

FIG. 3 reports the temperature differential which resulted between the two thermocouples of the sensor as a function of adding increasing amounts of isopentane ($C_5H_{12}$) to the initial gas; in each case the amount of $N_2$ was modified in order to maintain the constant total flow rate of 7508 cc/min. The data shows a strong linear dependence of the $\Delta T$ signal as the concentration of isopentane in the reaction gas increases from zero to 1000 ppm.

Figure 4:
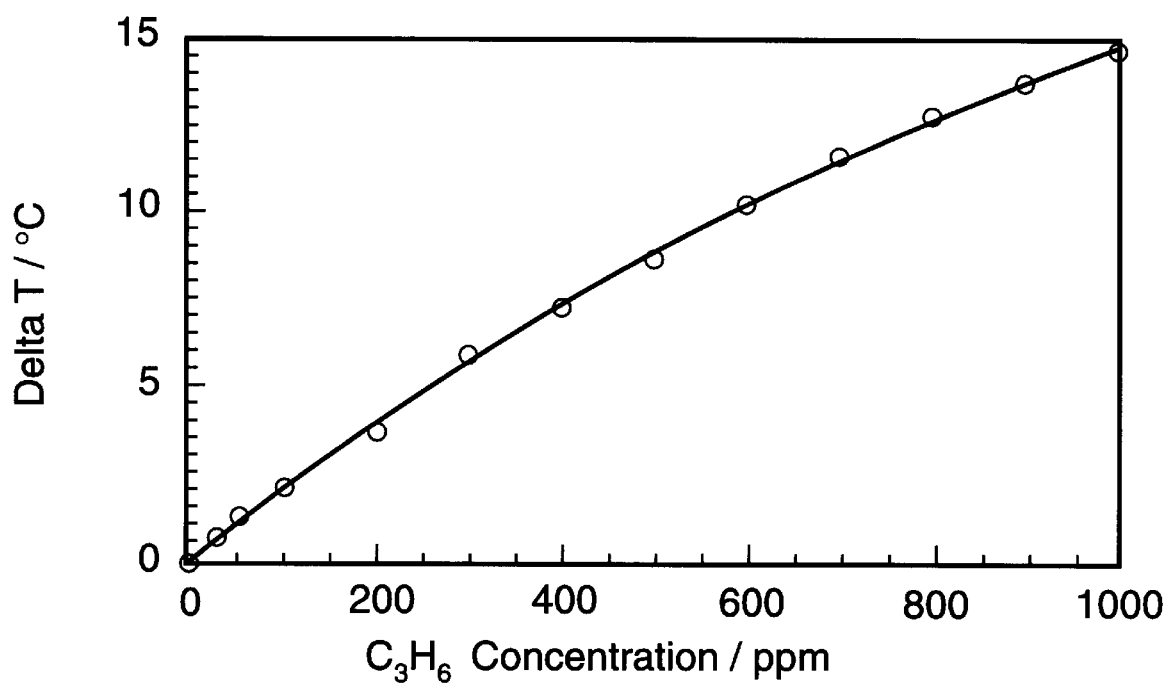
FIG. 4 is a graphical illustration of the temperature change ($\Delta T$) between a catalytic and reference thermocouple of a divided sensor device a function of the propylene (1-propene) concentration.

FIG. 4 reports the temperature differential which resulted between the two thermocouples of the sensor as a function of adding increasing amounts of propylene ($C_3H_6$) to the initial gas; the $N_2$ amount was again modified as the propylene concentration was increased thereby maintaining a constant total flow rate of 7508 cc/min. Once again the data shows a strong linear dependence of the $\Delta T$ signal as the concentration of propylene in the reaction gas increases from zero to 1000 ppm.

Figure 5:
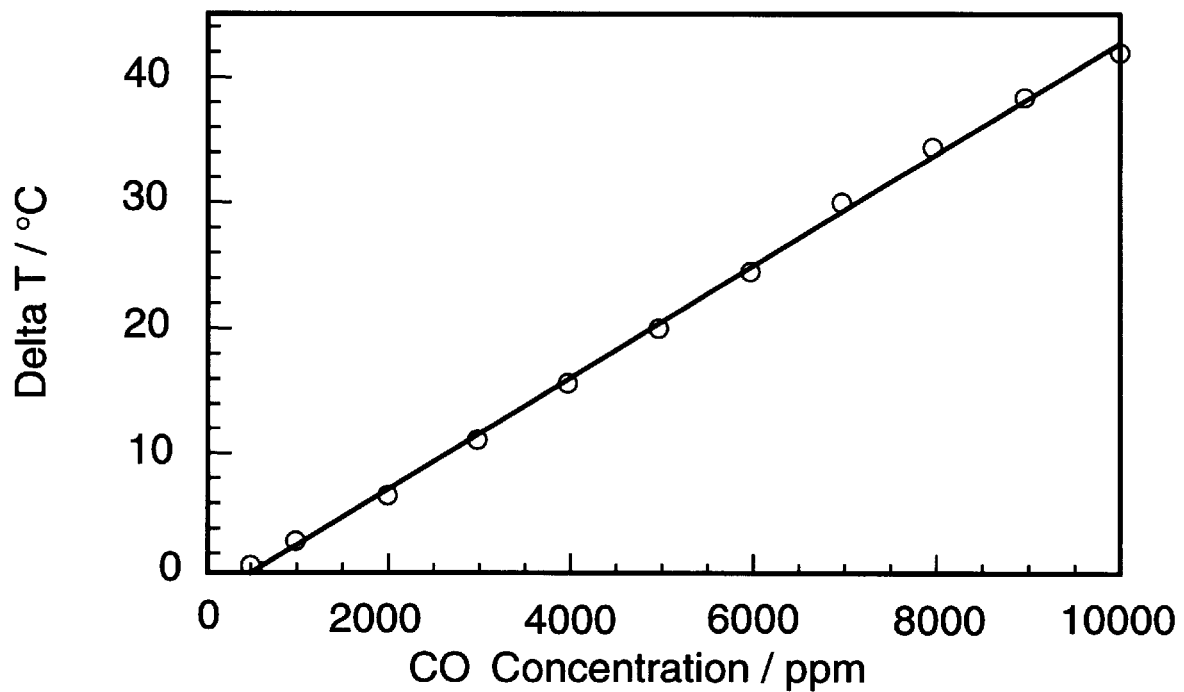
FIG. 5 is a graphical illustration of the temperature change ($\Delta T$) between a catalytic and reference thermocouple of a divided sensor device as a function of the carbon monoxide concentration.

FIG. 5 reports the temperature differential which resulted between the two thermocouples of the sensor as a function of adding increasing amounts of carbon monoxide (CO) to the initial gas; as before the $N_2$ amount was adjusted as the CO concentration increased to maintain the constant 7508 cc/in flow. Examination of the data again shows a clear linear dependence of the $\Delta T$ signal as the concentration of CO in the reaction gas increases from zero to 10000 ppm.

The linear dependence of the $\Delta T$ signal as the concentration of gas increases, which is shown for each of the above FIGS. and test gases, demonstrates both the ability to readily calibrate a $\Delta T$ output signal representative of the oxidation exotherm effect discussed above and to measure the HC concentration over a wide range of HC concentrations below 1000 ppm. Furthermore, the above data/FIGS. support the proposition that the invention is not specific to just one HC or only one HC family as both alkanes and alkenes are shown as being readily catalyzed ty the oxidation catalyst.

Example 2

The second or "selective" sensor, i.e. one which preferentially catalyzes carbon monoxide, was prepared and tested in the following manner:

Formation of the catalyst-support material/catalytically active precious metal mixture first involved forming 30 mg of a rhodium chloride solution (10%, by weight, Rh) by adding rhodium chloride powder, as supplied by the Aldrich Chemical Company Inc., Milwaukee, Wis, to the necessary amount of water. This rhodium chloride solution was dissolved into a sufficient amount of ammonia hydroxide solution to form 30 mls of a second solution having a pH of 12. 10 g of a fumed silica material, manufactured and sold by the Degussa Corporation, Ridgefield Park, N.J., as AEROSIL 130, was thereafter added to the 30 mls of the rhodium-chloride ammonium solution, i.e., incipient wetness or capillary impregnated, and mixed to form a silica slurry, which was thereafter dried in an oven for one day at a temperature of 130° C. The dried powder was first, calcined and reduced for one hour at a temperature of 300° C. in an atmosphere consisting of 6% $H_2/N_2$ and thereafter calcined in a flowing air atmosphere for 4 hours at a temperature of 500° C.

The actual divided sensor device was thereafter formed in the following manner:

An aqueous slurry comprised of the above calcined powder was formed and thereafter dip-coated as a 1 mm³ bead onto the tip of a type-K thermocouple, i.e., the first catalyzed portion. The second oxidation-catalyst-free portion also comprised a type K thermocouple which was dip-coated to form a 1 mm³ bead, however the bead consisted of a high surface area catalytically-inactive $SiO_2$ material. Both coated thermocouples were dried as above.

The testing of the "selective" sensor was performed in the same manner as for the "predominate oxidation species" sensor; i.e. tubular flow-through reactor, multi-pin feedthrough, 7508 cc/min total flow, introduction of gases via mass flow controllers, one minor difference being was that the furnace was maintained at 360° C. resulting in a thermocouple temperature of 270° C. Again the base or initial reaction, gas to which the various test gases (see Table II below) were added, consisted of 14% $CO_2$, 1% $O_2$, the balance comprising $N_2$.

Various concentrations of CO, propylene (alkene HC), isopentane (alkane HC), and toluene (aromatic HC) were introduced into the reactor with $N_2$ flow again adjusted to maintain constant total flow rate. Table II reports the various concentrations of these gases, in parts per million (ppm), and the reaction rate of the gases on the catalyst surface as monitored by the temperature difference between the catalyzed and un-catalyzed thermocouples ($\Delta T$).

TABLE II

| Test No. | Concentration of Test Gas Added (ppm) | $\Delta T$ (° C.) |
|---|---|---|
| 1 | 10,000 ppm CO | 35 |
| 2 | 1000 ppm $C_3H_6$ | 5 |
| 3 | 500 ppm toluene | 0 |
| 4 | 1000 ppm isopentane | 0 |

An examination of Table II reveals the following. (1) test sample 1, the presence of 10,000 ppm CO in the exhaust, produced a temperature rise, or $\Delta T$, of 35° C. indicating significant amount of CO being oxidized, (2) test sample 2, the presence of 1000 ppm of the alkene, propylene, in the gas stream, produced a temperature rise of 5° C., indicating moderate activity of the catalyst for propylene; and, (3) test samples 3 and 4, the presence of 500 ppm of an aromatic hydrocarbon, toluene, and 1000 ppm of an alkane, isopentane, respectively, produce no temperature change indicating the catalysts has no activity for isopentane and toluene. In sum, this sensor selectively catalyzes CO and alkenes, but is inactive for aromatic and alkane hydrocarbons; i.e., a "CO selective" sensor.

Although the now preferred embodiments of the invention have been set forth, it will be apparent to those skilled in the art that various changes and modifications may be made thereto without departing from the spirit and scope of the invention as set forth in the following claims.

We claim:

1. A system for measuring the hydrocarbon concentration of a gas sample, comprising:

a first catalytic differential calorimetric sensor, capable of producing a first output signal representative of the exothermic effect of the oxidation of the predominate oxidizable species in a gas samples, the predominate oxidizable species comprising the combination of $CO+H_2$+non-methane hydrocarbons;

a second catalytic differential calorimetric sensor, capable of producing a second output signal representative of the exothermic effect of the oxidation of the $CO+H_2$+alkene hydrocarbons species in the gas sample; and, a heater for maintaining each of the first and second differential catalytic calorimetric sensors at a temperature sufficient to effect substantially complete oxidation of the predominate oxidizable species and the $C+H_2$+alkene hydrocarbons species, respectively;

a means for comparing the first output signal with the second output signal to indicate the total concentration of unburned aromatic and alkane hydrocarbons and thus the total non-methane hydrocarbons in the gas sample.

2. The system of claim 1 wherein the first catalytic differential calorimetric sensor comprises a substrate having a first catalytic portion having an oxidation catalyst capable of oxidizing the predominate oxidizable species in the gas sample and an adjacent second reference portion which is oxidation catalyst-free and the second catalytic differential calorimetric sensor comprises a substrate having a first catalytic portion having an oxidation catalyst capable of selectively oxidizing the $CO+H_2$+alkene hydrocarbon species in the gas sample and an adjacent second reference portion which is oxidation catalyst-free.

3. The system of claim 2 wherein the first and second sensors each includes means for measuring the temperature of the first catalyzed portion and the second catalyst-free reference portion.

4. The system of claim 3 wherein the means of measuring the temperature is selected from the group consisting of thermocouples, thermistors and resistance temperature devices.

5. The system of claim 4 wherein the heater for each of the first and second differential catalytic calorimetric sensors and the means for measuring the temperature comprises a resistance temperature device.

6. The system of claim 2 wherein the first and second sensor device oxidation catalyst comprises a high surface area catalyst-support material and a catalytically active precious metal material.

7. The system of claim 6 wherein the catalyst-support material is comprised of a material selected from the group consisting of alumina, zirconia, silica, ceria, titania and mixtures thereof.

8. The system of claim 6 wherein the precious metal is selected from the group consisting of rhodium, platinum, palladium, iridium, silver, gold, ruthenium, osmium, and mixtures thereof.

9. The system of claim 6 wherein the first sensor device oxidation catalyst is comprised of a ceria/zirconia solid solution catalyst-support material and the precious metal comprises platinum.

10. The system of claim 6 wherein the second sensor oxidation catalyst is comprised of a high surface area silica catalyst-support material and the precious metal comprises rhodium.

11. The system of claim 10 wherein oxidation catalyst comprises an amount of highly dispersed rhodium cluster deposits on the surface of a high surface area catalyst-support material, the rhodium cluster deposits comprising a single rhodium atom or a cluster of at least two rhodium atoms, the deposits having a diameter of less than about 5 nm and covering no greater than about 10% of the surface area of the catalyst-support material.

12. A method of measuring the hydrocarbon concentration of an exhaust gas comprising the steps of:

(1) contacting a first portion of the exhaust gas with a first sensor producing an output signal representative of the concentration of the predominate oxidizable species in the first exhaust gas portion, the predominate oxidizable species comprising the combination of $CO+H_2+$ non-methane HCs;

(2) contacting a second portion of the exhaust gas with a second sensor producing a second output signal representative of the combined concentration of the $CO+H_2+$alkene species in the second exhaust gas portion;

(3) comparing the first output signal with the second output signal thereby determining the concentration of the aromatic and alkane hydrocarbon species in the exhaust gas and thereafter analyzing the concentration of the aromatic and alkane hydrocarbon species to determine the concentration of the total non-methane hydrocarbon species.

13. The method of claim 12 wherein step 2 involves a second catalytic differential calorimetric sensor selectively oxidizing a combination of $CO+H_2+$alkene oxidizable species in the second exhaust gas portion, and thereafter producing a output signal representative of the exothermic effect of the second oxidation.

14. The method of claim 12 involving producing a temperature differential as the output signal.

15. The method of claim of claim 12 wherein the exhaust gas is part of an exhaust stream produced by an internal combustion engine and the contacting of steps 1 and 2 is performed downstream of a catalytic converter.

16. The method of claim 12 wherein step 1 involves a first catalytic differential calorimetric sensor catalytically oxidizing the predominate oxidizable species in the first exhaust gas portion and thereafter producing an output signal representative of the exothermic effect of the oxidation.

17. The method of claim 16 involving producing a temperature differential as the output signal.

* * * * *

UNITED STATES PATENT AND TRADEMARK OFFICE
CERTIFICATE OF CORRECTION

PATENT NO. : 6,037,183
DATED : March 14, 2000
INVENTOR(S) : Faber et al.

It is certified that error appears in the above-identified patent and that said Letters Patent is hereby corrected as shown below:

Column 1,
Line 67, "warned" should be -- warmed --.

Column 10,
Line 9, "alkare" should be -- alkane --.

Column 12,
Line 26, "cc/in" should be -- cc/min --.
Line 38, "ty" should be -- by --.

Column 13,
Line 61, "samples" should be -- sample --.

Column 14,
Line 4, "$C+H_2+alkene$" should be -- $CO+H_2+alkene$ --.

Signed and Sealed this

Twenty-third Day of October, 2001

Attest:

*Nicholas P. Godici*

NICHOLAS P. GODICI
*Attesting Officer*    *Acting Director of the United States Patent and Trademark Office*